(12) United States Patent
Olson et al.

(10) Patent No.: US 7,776,832 B2
(45) Date of Patent: Aug. 17, 2010

(54) ANTICANCER TREATMENT WITH A COMBINATION OF TAXANES AND 13-DEOXYANTHRACYCLINES

(75) Inventors: Richard D. Olson, Nampa, ID (US); Gerald M. Walsh, Birmingham, AL (US)

(73) Assignee: Gem Pharmaceuticals, LLC, Birmingham, AL (US)

( * ) Notice: Subject to any disclaimer, the term of this patent is extended or adjusted under 35 U.S.C. 154(b) by 226 days.

(21) Appl. No.: 11/408,000

(22) Filed: Apr. 21, 2006

(65) Prior Publication Data

US 2007/0249547 A1  Oct. 25, 2007

(51) Int. Cl.
*A01N 43/04* (2006.01)
*A61K 31/70* (2006.01)

(52) U.S. Cl. .............................. 514/33; 514/34; 514/35

(58) Field of Classification Search ........................ None
See application file for complete search history.

(56) References Cited

FOREIGN PATENT DOCUMENTS

WO    WO-0066093 A2    11/2000

OTHER PUBLICATIONS

Nabholtz et al. Journal of Clinical Oncology (2003), vol. 21, pp. 968-975.*
Gambliel et al. Biochemical and Biophysical Research Communications (2002), vol. 291, pp. 433-438.*
Piccart-Gebhart MJ, et al, "Taxanes Alone or in Combination With Anthracyclines as First-Line Therapy of Patients With Metastic Breast Cancer", J. Clin Oncol, Apr. 20, 2008, 26 (12): 1980-6 (Abstract).
Sledge GW, et al, "Phase III Trial of Doxorubicin, Paclitaxel, and the Combination of Doxorubicin and Paclitaxel as Front-Line Chemotherapy for Mestastatic Breast Cancer: An Intergroup Trial (E1193)," J. Clin Oncol, Feb. 15, 2003; 21(4):588-92 (Abstract).

* cited by examiner

*Primary Examiner*—Patrick T Lewis
(74) *Attorney, Agent, or Firm*—Connolly Bove Lodge & Hutz LLP

(57) ABSTRACT

A 13-deoxy anthracycline and a taxane can be administered to a patient simultaneously, separately, sequentially, or consecutively to produce a therapeutic anticancer effect with reduced toxicity and side effect profile, compared to the administration of equieffective amounts of either compound alone. A composition or preparation of a 13-deoxy anthracyclines and a taxane for producing a potent anticancer therapeutic effect is also provided.

21 Claims, 4 Drawing Sheets

ANTICANCER TREATMENT WITH A COMBINATION OF TAXANES AND 13-DEOXYANTHRACYCLINES

TECHNICAL FIELD

The present disclosure relates to an anticancer treatment by administering a taxane such as paclitaxel or docetaxel and a 13-deoxy anthracycline. The present disclosure makes it possible to achieve an enhanced anticancer effect without cumulative irreversible cardiotoxicity. The present disclosure also relates to compositions comprising a taxane and a 13-deoxy-anthracycline.

BACKGROUND

The most well-known anthracycline anticancer drugs are doxorubicin and daunorubicin, which contain a 13-keto group. Doxorubicin, disclosed in U.S. Pat. No. 3,590,028, has a wide spectrum of anticancer utility and is used in the treatment of leukemias, lymphomas, and solid tumors. Daunorubicin, disclosed in U.S. Pat. No. 3,616,242, is useful in the treatment of acute leukemias. However, the utility of these drugs is limited by a serious side effect of cardiotoxicity so that the total amount of drug that can be given to a patient cannot exceed 550 mg/$M^2$ (E. A. Lefrak et al., Cancer, 32:302, 1973). Even at or near the recommended maximum total cumulative dosage (430-650 mg/$M^2$) significant and persistent heart dysfunction occurs in 60% of patients and 14% develop congestive heart failure. (A. Dresdale et al., Cancer, 52:51, 1983). Thus, while these drugs are useful to inhibit the growth of cancerous tumors, the patient may die of congestive heart failure because of the severe cardiotoxic side effect of the drugs.

It has also been found that the cardiotoxicity of these anthracyclines is produced by the metabolic reduction of the 13-keto moiety to a 13-dihydro alcohol metabolite (P. S. Mushlin et al., Fed. Proc., 45:809, 1986). In test systems where doxorubicin is not metabolized appreciably to the 13-dihydro alcohol metabolite (doxorubicinol) no significant cardiotoxic effects are observed (P. S. Mushlin et al., Fed. Proc., 44:1274, 1985; R. D. Olson et al., Fed. Proc., 45:809, 1986). In contrast, the 13-dihydro metabolites, doxorubicinol and daunorubicinol, produce cardiotoxicity in these same test systems at relatively low concentrations (1-2 micrograms/ml, R. D. Olson et al., Proceed. Am. Assoc. Cancer Res., 26:227, 1985; R. D. Olson et al., Proceed Am. Assoc. Cancer Res. 28:441, 1987).

If doxorubicin is allowed to remain in the test systems even for short periods of time some metabolic conversion occurs and the 13-dihydro metabolite is formed in sufficient quantity so that cardiotoxicity begins to develop (L. Rossini et al., Arch. Toxicol. Suppl., 9:474, 1986; M. Del Tocca et al., Pharmacol. Res. Commun., 17:1073, 1985). Substantial evidence has, thus, accumulated that the cardiotoxicity of drugs such as doxorubicin and daunorubicin results from the potent cardiotoxic effects produced by their 13-dihydro metabolites (P. Mushlin et al., FASEB Journal, 2:A1133, 1988; R. Boucek et al., J. Biol. Chem., 262:15851, 1987; and R. Olson et al., Proc. Natl. Acad. Sci., 85:3585, 1988; Forrest G L, et al., Cancer Res 60:5158, 2000).

It is known that doxorubicin in combination with the taxanes, such as paclitaxel, produces an enhanced anticancer effect in breast cancer, compared to either drug alone. Anticancer response rates with doxorubicin alone in breast cancer are 35-50%. With paclitaxel alone the response rate is 32-62%. However, in combination, these two drugs can produce response rates of 83-94% (Gianni L, et al., J Clin Oncol. 13:2688, 1995. Dombernowsk; P et al., Seminars in Oncology 23:23, 1996). Unfortunately, the combination of paclitaxel and doxorubicin can cause clinical congestive heart failure in 18-20% of patients (Gianni L, et al., J Clin Oncol. 13:2688, 1995; and Dombernowsk; P et al., Seminars in Oncology 23:23, 1996). Paclitaxel enhances the cardiotoxicity of doxorubicin which limits or precludes the use of anthracyclines in combination with taxanes. The incidence of congestive heart failure can be limited by reducing the dose of doxorubicin (Giordano S H et al., Clin Cancer Res 8:3360, 2002), but the efficacy of the combination can also be thereby reduced (Sparano J A et al., J Cin Oncol 17: 3828, 1999; Valero V, et al., Semi Oncol 28:15. 2001). In addition, even low doses of doxorubicin in combination with paclitaxel cause cardiotoxicity as demonstrated by reductions in left ventricular ejection fraction (Sparano J A et al., J Cin Oncol 17: 3828, 1999).

SUMMARY OF THE INVENTION

The present disclosure overcomes prior art problems and provides an anticancer combination therapy that comprises using certain anthracyclines which when combined with the taxanes will not produce or at least significantly reduces cardiotoxicity and avoid an unacceptable risk of congestive heart failure. This in turn provides significant improvement in the treatment of cancers including breast cancer as compared to existing therapies.

The present disclosure is concerned with a method for treating cancer which comprises administering to a mammal, including a human, in need thereof, a therapeutically effective amount of a 13-deoxy anthracycline of the following formula:

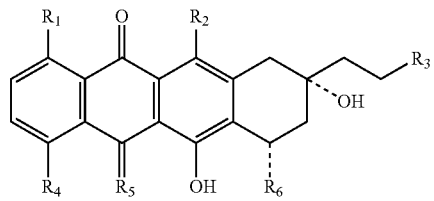

wherein each $R_1$, $R_2$ and $R_3$ individually is H or OH;

$R_4$ is H, OH, alkyl, or O-alkyl;

$R_5$ is O or NH; and $R_6$ is a sugar moiety; pharmaceutically acceptable salts thereof, prodrugs thereof and mixtures;

and a therapeutically effective amount of a taxane. The method of this disclosure can be carried out wherein the 13-deoxy anthracycline and taxane are administered simultaneously, separately in either order, sequentially in either order, or consecutively in either order to provide an anticancer effect.

Another aspect of the present disclosure relates to a composition that provides an anticancer, antitumor, and/or anitneoplastic effect useful in the treatment of cancers. The compositions of the present disclosure comprise a 13-deoxy anthracycline compound represented by the formula X:

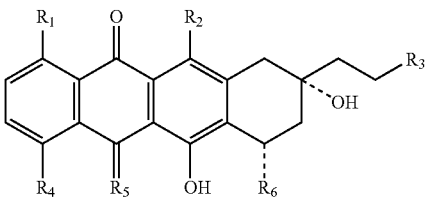

wherein
each $R_1$, $R_2$ and $R_3$ individually is H or OH;
$R_4$ is H, OH, alkyl, or O-alkyl;
$R_5$ is O or NH; and
$R_6$ is a sugar moiety, pharmaceutically acceptable salts thereof and prodrugs thereof; and a taxane compound, such as paclitaxel or docetaxel.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

DETAILED DESCRIPTION OF THE PREFERRED EMBODIMENTS

Figure 1:
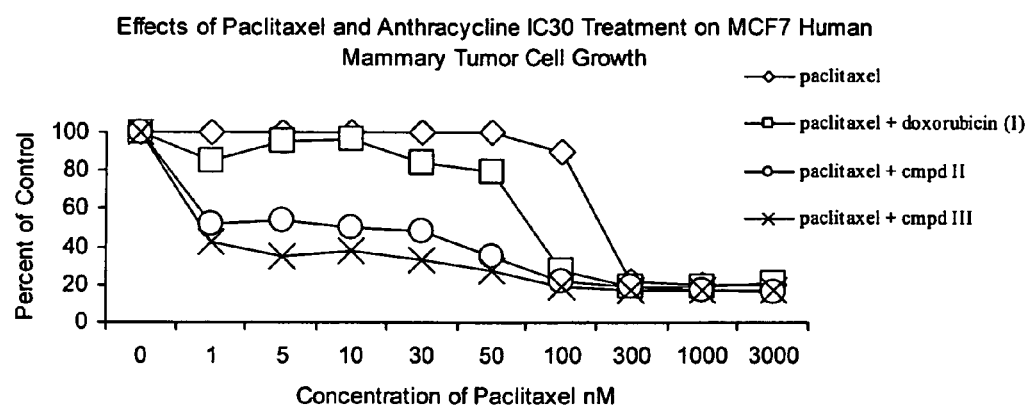
FIGS. 1 and 2 illustrate the dose-response relationships for paclitaxel on the inhibition of growth of MCF-7 cells, alone and in the presence of the IC30 concentrations of doxorubicin, daunorubicin, or 13-deoxy anthracycline compounds according to the present disclosure.

While the following description details certain embodiments of the present disclosure, it is to be understood that the disclosure is not limited in its application to the details of compositions and combinations of the compounds described in the accompanying examples and experiments, since the disclosure is capable of other embodiments and of being practiced in various ways.

The 13-deoxy anthracycline compounds employed according to the present disclosure have the following formula X:

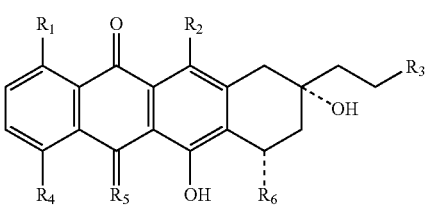

Wherein
each $R_1$, $R_2$ and $R_3$ individually is H or OH;
$R_4$ is H, OH, alkyl, or O-alkyl;
$R_5$ is O or NH; and
$R_6$ is a sugar moiety; pharmaceutically acceptable salts thereof and prodrugs thereof.

The more typical sugar moieties are daunosamine, epidaunosamine, or a rhamnal sugar. The more typical 13-deoxy compounds are 13-deoxydoxorubicin, 13-deoxydaunorubicin, 13-deoxycarminomycin, 13-deoxyepirubicin, 13-deoxyidarubicin, 13-deoxyannamycin, and the 5-imino analogs thereof.

The combination therapy according to this disclosure further comprises employing a taxane. More typical taxanes are paclitaxel and docetaxel; pharmaceutically acceptable salts thereof and prodrugs thereof.

The compounds according to this disclosure may form prodrugs at hydroxyl or amino functionalities using alkoxy, amino acids, etc. groups as the prodrug forming moieties. For instance, a hydroxymethyl a the 4 position may form mono-, di- or triphosphates and again these phosphates can form prodrugs. Hydroxy and hydroxymethyl groups may be converted to —$OCH_2P(O)(OH)_2$ and the prodrugs of phosphonates. The oxygen atom of a hydroxymethyl may be converted to $CH_2$ and then to $CH_2P(O)(OH)_2$ and the prodrugs.

Prodrug forms of the compounds bearing various nitrogen functions (amino, hydroxyamino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined earlier.
(a) Carboxamides, —NHC(O)R
(b) Carbamates, —NHC(O)OR
(c) (Acyloxy)alkyl Carbamates, NHC(O)OROC(O)R
(d) Enamines, —NHCR(=CHCO$_2$R) or —NHCR (=CHCONR$_2$)
(e) Schiff Bases, —N=CR$_2$
(f) Mannich Bases (from carboximide compounds), RCONHCH$_2$NR$_2$ Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the disclosure.

Prodrug forms of carboxyl-bearing compounds of the disclosure include esters (—CO$_2$R) where the R group corresponds to any alcohol whose release in the body through enzymatic or hydrolytic processes would be at pharmaceutically acceptable levels. Another prodrug derived from a carboxylic acid form of the disclosure may be a quaternary salt type

of structure described by Bodor et al., J. Med. Chem. 1980, 23, 469.

Pharmaceutically acceptable salts of the compounds of the present disclosure include those derived from pharmaceutically acceptable inorganic or organic acids. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include alkali such as sodium and ammonia.

Recently it has been discovered that the 13-deoxy forms of doxorubicin, daunorubicin, or other similar anthracyclines will not be metabolically converted to cardiotoxic 13-dihydro forms, and are, therefore, devoid of cumulative irreversible cardiotoxicity. In particular, see WO99/08687, U.S. Pat. Nos. 5,948,896 and 5,942,605 and PCT/US99/04704, disclosures of which are incorporated herein by reference. Heretofore it has been unknown whether such anthracyline anticancer agents would have an enhanced or even synergistic anticancer effect in combination with taxanes.

Along these lines, the IC50 of paclitaxel alone for inhibition of MCF-7 human mammary tumor cell growth is 221 nM. In the presence of weak growth inhibitory concentrations of 13-deoxy anthracyclines of the present disclosure, the IC50 of paclitaxel decreases to 0.55-11 nM. Paclitaxel alone has no inhibitory activity on P388 murine leukemia cell growth, but in the presence of weak growth inhibitory concentrations of the 13-deoxy anthracyclines, the IC50 of paclitaxel is 13-20 nM. In non-cancerous rat-derived H9c2 cells, weak growth inhibitory concentrations of paclitaxel (IC10) decrease the IC50 of 13-deoxydoxorubicin from 700 nM to 400 nM, decrease the IC50 of 13-deoxy-5-iminodoxorubicin from 1500 nM to 210 nM, but does not reduce the IC50 of doxorubicin which remains the same at 210 nM. 13-deoxy anthracyclines of the present disclosure, when combined with taxanes produce an enhanced, highly potent anticancer, antitumor, and/or antineoplastic effect.

The present disclosure makes possible a potentiation of the anticancer, antitumor, and/or antineoplastic efficacy of taxanes by low doses of 13-deoxy anthracyclines of the formula of the present disclosure. Moreover, compositions according to the present disclosure, comprising a taxane and a 13-deoxy anthracycline, are devoid of or have significantly reduced cardiotoxicity. The present disclosure in the use of a combination of a taxane and a 13-deoxy anthracycline can provide for an efficacious treatment at reduced doses compared to those required when each drug is used alone.

Moreover, use of the taxane combined with a 13-deoxy anthracycline can provide a treatment which is safer and less toxic compared to each drug used alone. It is important to note that the 13-deoxy anthracycline and taxane can be used simultaneously, separately or consecutively.

In addition, the treatment of the present disclosure employing the combination of 13-deoxy anthracyclines and taxanes, exhibits anticancer, antitumor, and/or neoplastic efficacy, that are useful for all types of therapies for treating cancers, neoplasms, or tumors, including leukemia, melanoma, liver, breast, ovary, prostate, stomach, pancreas, lung, kidney, colon, and central nervous system tumors. The treatment of the present disclosure provides a method of suppressing the growth of cancers, tumors, and/or neoplasms in mammals, including humans.

A typical composition, combination, mixture, or preparation of the constituents according to the disclosure is a compound of formula X combined with paclitaxel or docetaxel. A more typical composition, combination, mixture, or preparation is a 13-deoxy anthracycline selected from the group consisting of 13-deoxydoxorubicin, 13-deoxydaunorubicin, 13-deoxyepirubicin, 13-deoxyidarubicin, 13-deoxyannamycin, 13-deoxycarminomycin, 13-deoxyamrubicin and the 5-imino analogs thereof, in combination with paclitaxel or docetaxel.

The constituents of the composition, combination, mixture, or preparation can be administered to a patient simultaneously, separately, sequentially, or consecutively. The constituents can be administered to a patient in any acceptable manner that is medically acceptable, including orally, parenterally, topically, or by implantation. Oral administration includes administering the constituents of the compositions, combinations, mixtures, or preparations in the form of tablets, capsules, lozenges, suspensions, solutions, emulsions, powders, syrups, and the like. The preferred route of administration is parenteral.

The actual method and order of administration of the constituents may vary according to the particular pharmaceutical formulation of the 13-deoxy anthracycline of formula X being utilized, the particular pharmaceutical formulation of the taxane being utilized, the particular cancer being treated, the severity of the disease state being treated, and the particular patient being treated. The dosage ranges for the administration of the constituents may vary with the age, condition, sex, and extent of the disease in the patient, and can be determined by one of ordinary skill in the art.

A pharmaceutical composition of the present disclosure comprises a 13-deoxy anthracycline of formula X mixed together with a taxane in a pharmaceutically acceptable carrier or excipient. These pharmaceutical compositions of the present disclosure are useful in anticancer therapy.

The pharmaceutically acceptable carriers or excipients are well known to those having ordinary skill in the art of formulating compounds in a form of pharmaceutical compositions, combinations, mixtures, and preparations. A pharmaceutically acceptable carrier refers to one or more compatible solid or liquid filler, diluent, or encapsulating substances which are suitable for administration to mammals including humans. Pharmaceutical compositions, combinations, mixtures, and preparations suitable for parenteral administration are formulated in a sterile form which may be a sterile solution or suspension in an acceptable diluent or solvent.

The amount of an active ingredient contained in the pharmaceutical composition may vary quite widely depending on many factors, such as the route of administration and the vehicle. In the present invention, a pharmaceutical composition may contain from about 0.1 to 1000 mg of a 13-deoxy anthracyclines of formula X, and from about 0.1 to 1000 mg of a taxane.

In the method of the subject disclosure, a 13-deoxy anthracycline of formula X is administered to a patient in need thereof at a dose from about 0.1 mg/m$^2$ body surface area to about 1000 mg/m$^2$ body surface area, more typically from about 10 mg/m$^2$ body surface area to about 500 mg/m$^2$ body surface area, and more typically by the parenteral route of administration. The taxane of the present disclosure is administered to a patient in need thereof at a dose from about 0.1 mg/m$^2$ to about 1000 mg/m$^2$, more typically from about 10 mg/m$^2$ to about 500 mg/m$^2$, and more typically by the parenteral route of administration. The 13-deoxy anthracycline and the taxane can be administered together, in a single composition, combination, mixture, or preparation, or can be administered separately in either order, sequentially in either order, or consecutively in either order. When not administered together, the second compound is typically administered within 72 hours of administering the first compound.

The anticancer therapeutic effects of the taxane are significantly increased by the 13-deoxy anthracycline of formula X without an increase in toxicity, due, in part, to the synergism between the taxane and the 13-deoxy anthracycline. The doses of the taxane and the 13-deoxy anthracyclines can be administered as frequently as necessary. The actual method and order of administration will vary according to the particular formulation, composition, combination, mixture, or preparation, the particular cancer being treated, and the particular patient being treated.

The enhanced actions of the combination of a 13-deoxy anthracycline with a taxane of the present disclosure are shown, by way of example, in the following tests, which are intended to illustrate but not to limit the present disclosure.

Anticancer Effects of 13-Deoxy Anthracyclines

The in vivo anticancer activities of doxorubicin (Compound I), 13-deoxydoxorubicin (compound II) and 5-imino-13-deoxydoxorubicin (compound III) are tested for anticancer activity in a murine leukemia model utilizing CD2F1 mice injected with P388 cells (mouse derived leukemia cancer cells). Groups of CD2F1 mice are injected intraperitoneally (ip) with 1 million P388 cells. There were 10 mice per group. In the doxorubicin group 0.8 mg/kg is administered ip consecutively for 9 days on days 1-9 of the study. 13-deoxydoxorubicin is administered ip at 1.6 mg/kg and 5-imino-13-deoxydoxorubicin ip at 3.2 mg/kg, in an identical fashion as for doxorubicin. A control group is injected with vehicle. Median survival times are calculated for each group. Activity of a compound is expressed as the amount of prolonged survival (median survival of the treated group divided by the median survival time of the control group, multiplied by 100, T/C %). The results are shown in Table 1. Doxorubicin produces an antitumor effect as shown by a significant 147% increase in median survival time. 13-deoxydoxorubicin and 5-imino-13-deoxydoxorubicin also produce a significant increase in median survival time, not significantly different from doxorubicin. The results of these studies demonstrate that 13-deoxy anthracyclines have anticancer efficacy similar to doxorubicin, although at different doses.

TABLE 1

Anticancer effects of doxorubicin and the 13-deoxyanthracyclines in mice with P388 murine leukemia (T/C = median survival time of treated mice divided by median survival time of control mice × 100; n = 10)

| Group | Dose mg/kg/day | Median survival time days | T/C % |
|---|---|---|---|
| Control | 0 | 19 | 100 |
| Doxorubicin (I) | 0.8 | 28 | 147* |
| Compound II | 1.6 | 27 | 142* |
| Compound III | 3.2 | 27 | 142* |

*p < .05 versus control

Cardiotoxicity Evaluation of 13-Deoxy Anthracyclines

Twenty-four age matched New Zealand white rabbits weighing 3.0 kg are randomized into four groups (N=6 rabbits/group). The groups are chronically treated with doxorubicin, 13-deoxydoxorubicin (II), 5-imino-13-deoxydoxorubicin (III), or vehicle (0.9% NaCl). Doses of drug or vehicle are administered iv into an ear vein two times per week. Serum and blood samples are obtained weekly and M-mode echocardiology performed weekly or every other week to obtain left ventricular fractional shortening (LVFS) to assess cardiac function. Food consumption is measured daily and body weight is measured weekly. Control rabbits are fed the same amount of food as doxorubicin treated rabbits (pair fed). At sacrifice, apex and left ventricular free wall samples are obtained and preserved in 10% buffered formalin for histologic scoring and analysis via light microscopy. Left ventricular tissue samples are also obtained to assess cardiac levels of anthracyclines and metabolites. Rabbits are sacrificed when they become cardiotoxic (LVFS<30% or decrease in LVFS by 10% units i.e., 42% to 32% LVFS), exhibit life threatening or debilitating toxicities (i.e., severe myelosupression or mucositis), or 13 weeks after beginning the study.

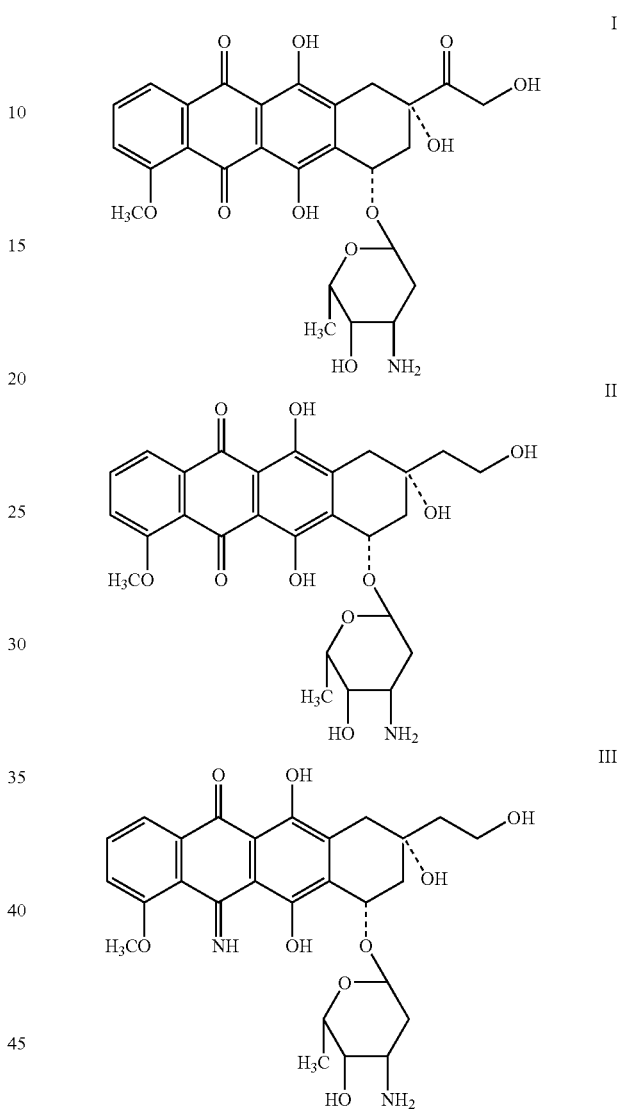

Optimum antitumor doses of 13-deoxydoxorubicin are approximately twice the dose of doxorubicin while those for 5-imino-13-deoxydoxorubicin are up to 7 times the optimum dose of doxorubicin. The dose of 13-deoxydoxorubicin and 5-imino-13-deoxydoxorubicin are, thus, twice (13-deoxydoxorubicin) and 7 times (5-imino-13-deoxydoxorubicin) the cumulative cardiotoxic dose of doxorubicin (17.5 mg/kg). Doxorubicin is administered 1.25 mg/kg twice/week for 7 weeks (cumulative dose of 17.5 mg/kg), 13-deoxydoxorubicin is administered 2 mg/kg twice/week for 10 weeks (cumulative dose of 40 mg/kg) and 5-imino-13-deoxydoxorubicin is administered 5 mg/kg twice/week for 12 weeks (cumulative dose of 120 mg/kg).

At sacrifice, the heart is removed and two types of tissue are sampled from the heart, ventricular apex and left ventricular free wall, and stored in 10% formalin. Each tissue is prepared for three different stains: H&E, toluidine blue, and trichrome. The tissues are scored (blind) using a modification of the Billingham scale. The scoring scale is from 0-4 with 0=<10% of cells or tissue lesioned, 1 to 10%-19% of cells or tissue lesioned, 2 to 20%-29% of cells or tissue lesioned, 3 to 30%-39% of cells or tissue lesioned, 4 to 40% or more cells or tissue lesioned. The ventricular apex and the left ventricular free wall are analyzed separately. Each receives a score for mononuclear infiltration, fibrosis, and cytoplasmic vacuolization. Thus, each rabbit has six scores, three for the apex (mononuclear infiltration, fibrosis, and cytoplasmic vacuolization) and three for the left ventricular free wall (mononuclear infiltration, fibrosis, and cytoplasmic vacuolization). Each score is obtained by looking at all three stains. The six scores are averaged for each rabbit to give an overall single score for each rabbit and then averaged for each treatment group.

Also at sacrifice, left atria are isolated, divided in half and both halves studied to assess cardiac function in vitro in a tissue bath where afterload and preload remain constant throughout the study. Cardiac contractility is measured as the maximum rate of force development (dF/dt) in response to contractions induced by electrical stimulation via punctate electrodes located at the base of each muscle preparation.

The results of these studies are presented in Table 2. Doxorubicin produces a statistically significant decrease in left ventricular fractional shortening (FS %) compared to vehicle controls and compared to the other two treatment groups. Compounds II and III do not alter left ventricular fractional shortening. All three drugs reduce hematocrit to the same extent, compared to vehicle controls. Myocardial contractility of isolated atria obtained at sacrifice and measured in vitro (dF/dt), is significantly reduced by doxorubicin, compared to vehicle controls and compared to the other two treatment groups. Compounds II and III do not alter myocardial contractility. Similarly, histopathologic lesions are significantly increased by doxorubicin, compared to vehicle controls and compared to the other two treatment groups, and compounds II and III do not produce histopathologic lesions. These results show that doxorubicin produces a profound cardiotoxicity in the rabbit with chronic dosing, but compounds II and III are devoid of cardiotoxicity in this model at doses comparable to those used with doxorubicin. This absence of cardiotoxicity with compounds II and III is believed to be due to the absence of a 13-keto group and the lack of formation of an alcohol metabolite.

Combination of Paclitaxel with 13-Deoxy Anthracyclines

The inhibitory effects of doxorubicin (I), 13-deoxydoxorubicin (II), 5-imino-13-deoxydoxorubicin (III), daunorubicin (IV), 13-deoxydaunorubicin (V), and 5-imino-13-deoxydaunorubicin (VI) on the growth of MCF-7 human mammary tumor cells and P388 murine leukemia cells are measured in vitro. The MCF-7 and P388 cell lines used for these studies are cultured and maintained utilizing the protocol from the American Type Culture Collection (ATCC) protocols. MCF-7 media was EMEM (Eagle Minimum

TABLE 2

Absence of cardiotoxic effects in rabbits treated chronically with 13-deoxyanthracyclines (values are means ± SE, n = 6)

|  | Control | | Doxorubicin (I) | | Compound II | | Compound III | |
| --- | --- | --- | --- | --- | --- | --- | --- | --- |
|  | Pre | Post | Pre | Post | Pre | Post | Pre | Post |
| FS % | 37.5 ± 0.3 | 36.8 ± 1.2 | 37.1 ± 0.4 | 27.4*,+ ± 1.8 | 38.1 ± 0.7 | 37.4 ± 1.0 | 37.3 ± 1.1 | 35.6 ± 0.7 |
| HCT % | 34.4 ± 0.4 | 38.7 ± 0.6 | 35.0 ± 0.5 | 27.5* ± 1.4 | 35.0 ± 0.7 | 23.8* ± 2.0 | 34.4 ± 0.7 | 33.3* ± 1.0 |
| dF/dt gms/sec; 3 Hz |  | 29.1 ± 4.3 |  | 15.1*,+ ± 1.9 |  | 24.4 ± 4.4 |  | 30.2 ± 4.9 |
| Histopathology Score |  | 0.97 ± 0.2 |  | 1.81*,+ ± 0.4 |  | 0.97 ± 0.1 |  | 0.64 ± 0.2 |

*p < .05 versus control; +p < .05 versus compound I and II; pre = pre-treatment, post = post-treatment.

Essential Medium; ATCC) and P388 media is Dulbecco's modified Eagle's medium (DMEM, ATCC). Working media for MCF-7 and P388 is made by the addition of 50 ml FBS (fetal bovine serum, MCF-7) or 50 ml horse serum (ATCC, P388) to 450 ml EMEM media (MCF-7) or DMEM (P388). 4.5 g/L glucose (Sigma) is also added to the DMEM (P388). Five ml Penecillin/Streptomycin (P/S, Gibco) is added to the MCF-7 and P388 working media. Cells are grown at 37° C. in 5% $CO_2$ for 1 week, and 25 ml fresh media is added. Cells are passaged when they reach a density of $1\text{-}2\times10^6$ cells/ml by transferring to a new flask containing fresh media.

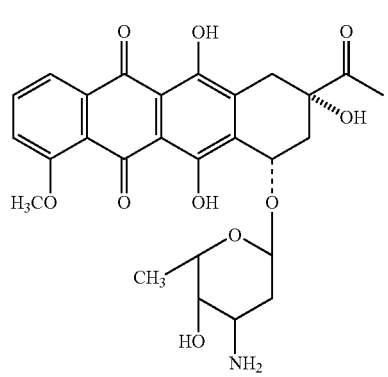

IV

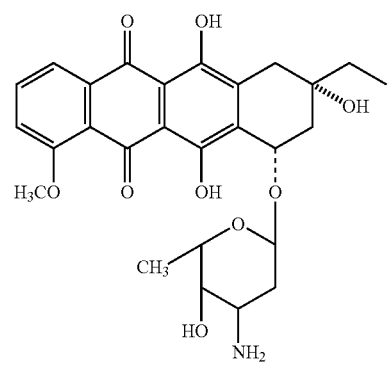

V

-continued

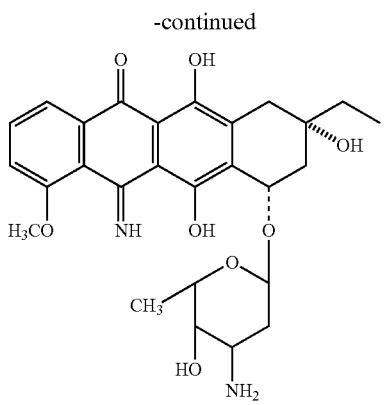

VI

Using sterile technique, MCF-7 cells are harvested from the T-75 flasks by removing and discarding the culture medium. 5 ml of 0.25% Trypsin-EDTA solution (Sigma) is added to each flask to de-attach the cells. The flask is placed in the incubator for 5-10 minutes to facilitate dispersal. 10 ml of complete growth medium is added, directly decanted into 50 ml tubes then centrifuged for 10 minutes at 200×g. P388 cells are harvested by directly decanting media into 50 ml tubes and centrifuging for 10 minutes at 200×g. The pellet (MCF-7 and P388) is resuspended in 5 ml and the cells dispersed by expelling gently through an 18 g needle fitted to a syringe. The cells are counted using a hemocytometer and diluted with media to 150,000 cells/ml. The diluted cells are pipetted into 96-well plates at a concentration of 15,000 cells/well in 100 µl. The plates are covered and incubated at 37° C. for 48 hours.

Dilutions of the anthracyclines and paclitaxel are made up in cell-specific serum-free media. The drugs at appropriate concentrations are added to all wells in 50 µl aliquots and the cells are grown in the presence of the drugs (anthracyclines/paclitaxel) for 24 hours. Tritiated thymidine (ICN) is diluted in serum-free cell-specific media to a concentration of 1 µCi/50 µl. All wells used for analysis are spiked with 50 µl aliquots of media containing tritiated thymidine. Following a 4-hour exposure to isotope, tritiated thymidine incorporation into DNA is measured by hypotonic lysis of cells with deionized water and collection of cellular contents onto Whatman GF-C filters using a Brandel cell harvester. Prior to harvesting MCF-7 cells, the media is aspirated, 150 µL of 0.25% Trypsin-EDTA is added to each well to de-attach the cells. Filters are allowed to dry, placed into 7 ml scintillation vials containing 5 ml scintillation cocktail and counted in a scintillation counter. In preliminary experiments, the concentrations of anthracyclines that would produce a 30% inhibition of growth (inhibitory concentration 30, IC30) on MCF-7 cells and 10% inhibition of growth (IC10) on P388 cells are determined. The results are shown in tables 3 and 4.

TABLE 3

IC30's of doxorubicin, daunorubicin, and the 13-deoxyanthracyclines for inhibition of growth of MCF-7 human mammary tumor cells

| | IC30 nM |
|---|---|
| Doxorubicin (I) | 100 |
| Compound II | 450 |
| Compound III | 750 |
| Daunorubicin (IV) | 750 |

TABLE 3-continued

IC30's of doxorubicin, daunorubicin, and the 13-deoxyanthracyclines for inhibition of growth of MCF-7 human mammary tumor cells

| | IC30 nM |
|---|---|
| Compound V | 645 |
| Compound VI | 875 |

TABLE 4

IC10's of doxorubicin, daunorubicin, and the 13-deoxyanthracyclines for inhibition of growth of P388 murine leukemia cells

| | IC10 nM |
|---|---|
| Doxorubicin (I) | 250 |
| Compound II | 1100 |
| Compound III | 3500 |
| Daunorubicin (IV) | 300 |
| Compound V | 700 |
| Compound VI | 1700 |

Figure 2:
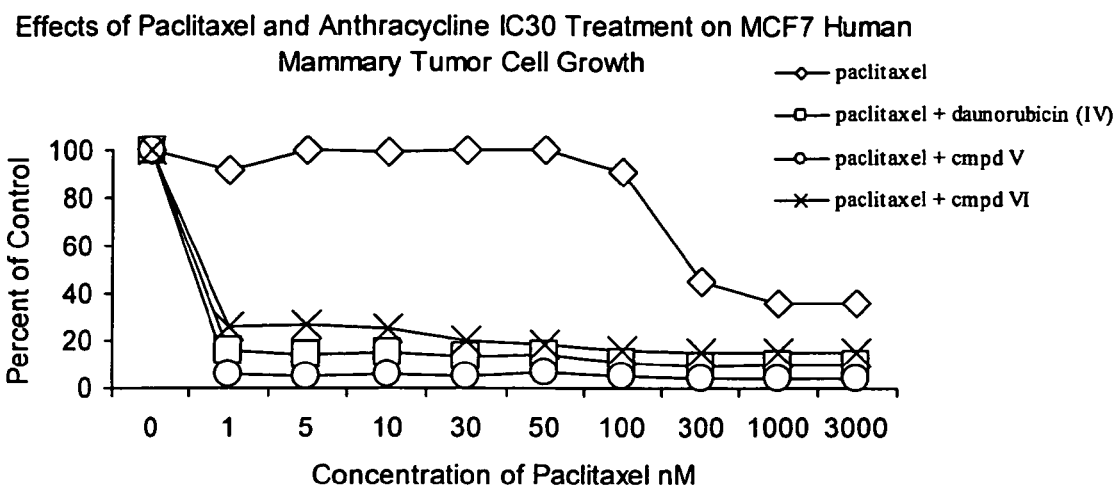

The dose-response relationships for paclitaxel on the inhibition of growth of MCF-7 cells, alone and in the presence of the IC30 concentrations of doxorubicin, daunorubicin, or compounds II, III, V, or VI are shown in FIGS. 1 and 2. From these dose-response curves, the IC50s for paclitaxel are calculated, and are presented in Table 5.

TABLE 5

IC50's (nM) of paclitaxel for inhibition of growth of MCF-7 human mammary tumor cells in the presence of doxorubicin, daunorubicin or 13-doxyanthracyclines at IC30 concentrations. Values are means ± standard errors, n = 3

| | IC50's (nM) of paclitaxel |
|---|---|
| Paclitaxel | 221 ± 8 |
| Paclitaxel + Doxorubicin (I) | 78 ± 6* |
| Paclitaxel + Compound II | 11 ± 9*,$^X$ |
| Paclitaxel + Compound III | 1 ± 0*,$^X$ |
| Paclitaxel + Daunorubicin (IV) | 0.6 ± 0*,$^X$ |
| Paclitaxel + Compound V | 0.55 ± 0*,$^X$ |
| Paclitaxel + Compound VI | 0.75*,$^X$ |

*$p < .05$ versus paclitaxel;
$^X p < .05$ versus paclitaxel + doxorubicin

Doxorubicin produces a 2.8 fold increase in the cancer growth inhibition potency of paclitaxel. Compound II produces a 20 fold increase and compound III a 220 fold increase. Daunorubicin and compounds V and VI produces increases in the growth inhibition potency of paclitaxel 295 to 400 fold. Compared to the other compounds, doxorubicin is a relatively weak potentiator of the cancer growth inhibition potency of paclitaxel.

Figure 3:
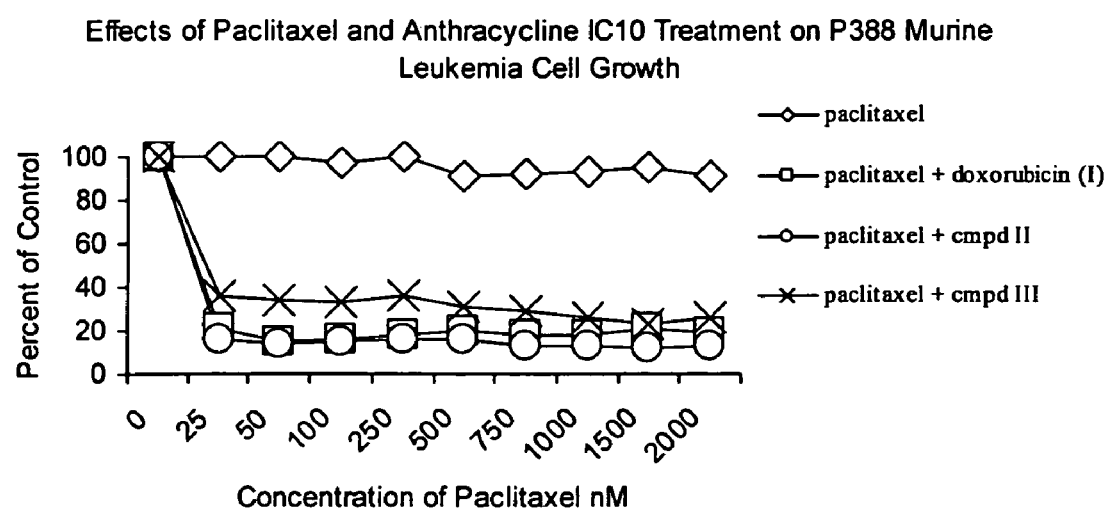
FIGS. 3 and 4 illustrate the dose-response relationships for paclitaxel on the inhibition of growth of P388 murine leukemia cells, alone and in the presence of the IC10 concentrations of doxorubicin, daunorubicin, or 13-deoxy anthracycline compounds according to the present disclosure.
Figure 4:
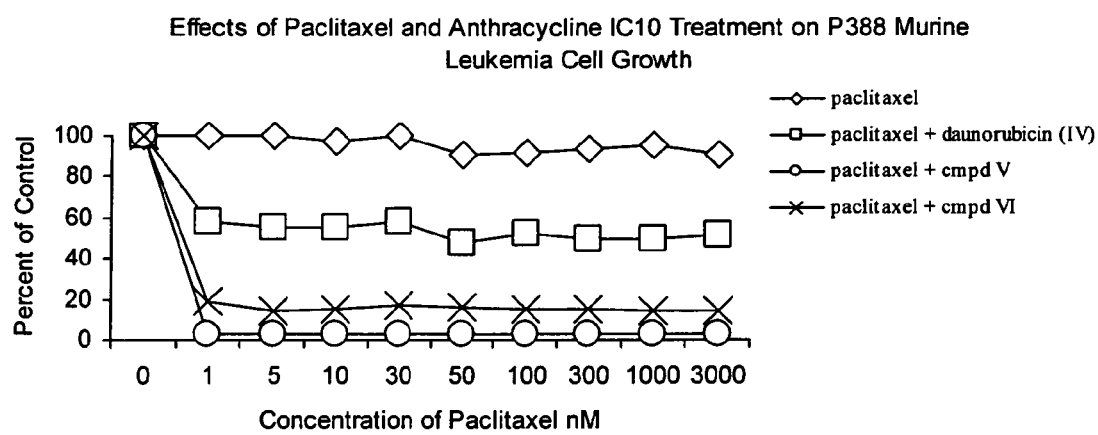

The dose-response relationships for paclitaxel on the inhibition of growth of P388 murine leukemia cells, alone and in the presence of the IC10 concentrations of doxorubicin, daunorubicin, or compounds II, III, V, or VI are shown in FIGS. 3 and 4. From these dose-response curves, the IC50s for paclitaxel are calculated, and are presented in Table 6.

TABLE 6

IC50's (nM) of paclitaxel for inhibition of growth of P388 murine leukemia cells in the presence of doxorubicin, daunorubicin or 13-doxyanthracyclines at IC10 concentrations. Values are means ± standard errors, n = 3

|  | IC50's (nM) of paclitaxel |
| --- | --- |
| Paclitaxel | Inactive |
| Paclitaxel + Doxorubicin (I) | 16 ± 0.58 |
| Paclitaxel + Compound II | 16 ± 0.50 |
| Paclitaxel + Comound III | 20 ± 0.67 |
| Paclitaxel + Daunorubicin (IV) | 916 ± 83* |
| Paclitaxel + Compound V | 13 ± 0 |
| Paclitaxel + Compound VI | 14 ± 0.83 |

*p < .05 versus compounds I, II, IV, V, and VI

Paclitaxel alone is inactive against P388 cells, producing no inhibition of growth. However, paclitaxel becomes a potent inhibitor of growth in the presence of the anthracyclines. The potency of paclitaxel is in the low nanomolar range in the presence of all the anthracyclines except daunorubicin, where its potency is in the high nanomolar range.

An enhanced effect occurs when the pharmacologic effect of the administration of the combination of two drugs is greater than the additive effects of the two drugs administered separately. For example, assume the dose of a first drug to produce a 30% response is 100 units and the dose of a second drug to produce a 30% response is 10 units. If 100 units of the first drug plus 10 units of the second drug produce a 60% response, then there is an additive effect between the two drugs. However, if 100 units of the first drug plus 10 units of the second drug produce a 90% response, then there is a synergistic or supradditive effect between the two drugs. Paclitaxel at concentrations in MCF7 cells that have no growth inhibitory effect (1 to 50 nM) will produce 50% to 95% inhibition of growth in the presence of concentrations of 13-deoxy anthracyclines of the formula of the present invention which inhibit growth only by 30%. Likewise, paclitaxel, which has no growth inhibitory effect on P388 cells at concentrations up to 2000 nM, will produce 65% to 95% inhibition of growth in the presence of concentrations of 13-deoxy anthracyclines of the formula of the present disclosure which inhibit growth only by 10%. Thus, the 13-deoxy anthracyclines of the present disclosure act in an enhanced manner or synergistically with paclitaxel to produce a highly potent and effective composition, combination, mixture or preparation for suppressing the growth of cancer cells.

The foregoing description has been limited to specific embodiments of this disclosure. It will be apparent, however, that variations and modifications may be made by those skilled in the art to the disclosed embodiments of the disclosure, with the attainment of some or all of its advantages and without departing from the spirit and scope of the present invention. For example, in non-cancerous rat-derived H9c2 cells, weak growth inhibitory concentrations of paclitaxel (IC10) decrease the IC50 of 13-deoxydoxorubicin from 700 nM to 400 nM, decrease the IC50 of 13-deoxy-5-iminodoxorubicin from 1500 nM to 210 nM, but do not reduce the IC50 of doxorubicin which remains the same at 210 nM. Thus, taxanes increase the potency of 13-deoxy anthracyclines. Suitable modifications and adaptations of a variety of conditions and parameters normally encountered in clinical therapy which are obvious to one of ordinary skill in the art are within the scope of the disclosure.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference.

What is claimed is:

1. A therapeutically effective amount of a synergistic anticancer combined preparation, in which the cancer is sensitive to a synergistic combination comprising a first compound and of a second compound, wherein:

the first compound is a 13-deoxyanthracycline, or pharmaceutically acceptable salts or prodrugs thereof, said 13-deoxyanthracycline having the formula:

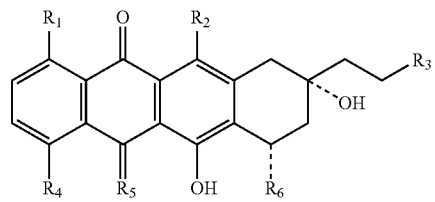

wherein
each of $R_1$, $R_2$ and $R_3$ is independently selected from the group consisting of H and OH;
$R_4$ is selected from the group consisting of H, OH, alkyl, and O-alkyl;
$R_5$ is selected from the group consisting of O and NH; and
$R_6$ is a sugar moiety; and
the second compound is a taxane.

2. The preparation of claim 1, wherein said 13-deoxyanthracycline is selected from the group consisting of 13-deoxydoxorubicin, 13-deoxydaunorubicin, 13-deoxycaminomycin, 13-deoxyepirubicin, 13-deoxyidarubicin, 13-deoxyannamycin, 13-deoxyamrubicin and the 5-imino analogs thereof, and said taxane is selected from the group consisting of paclitaxel and docetaxel.

3. A pharmaceutical composition comprising the preparation of claim 1, and a pharmaceutically acceptable carrier or excipient.

4. A pharmaceutical composition comprising the preparation of claim 2, and a pharmaceutically acceptable carrier or excipient.

5. The preparation of claim 1, wherein said sugar moiety is selected from the group consisting of daunosamine, epidaunosamine, and a rhamnal sugar.

6. A method for treating cancer comprising administering to a mammal in need thereof a therapeutically effective amount of a synergistic combination comprising:

(a) a 13-deoxyanthracycline, or pharmaceutically acceptable salts or prodrugs thereof, said 13-deoxyanthracycline having the formula:

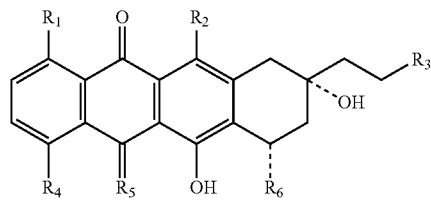

wherein
each of $R_1$, $R_2$ and $R_3$ is independently selected from the group consisting of H and OH;
$R_4$ is selected from the group consisting of H, OH, alkyl, and O-alkyl;
$R_5$ is selected from the group consisting of O and NH; and
$R_6$ is a sugar moiety; and
a taxane, wherein the 13-deoxyanthracycline and the taxane are administered simultaneously, separately, or sequentially to produce a synergistic anticancer effect, and wherein the cancer is sensitive to the synergistic combination.

7. The method of claim 6, wherein said sugar moiety is selected from the group consisting of daunosamine, epidaunosamine, and a rhamnal sugar.

8. The method of claim 6, wherein said 13-deoxyanthracycline is selected from the group consisting of 13-deoxydoxorubicin, 13-deoxydaunorubicin, 13-deoxycaminomycin, 13-deoxyepirubicin, 13-deoxyidarubicin, 13-deoxyannamycin, 13-deoxyamrubicin and the 5-imino analogs thereof, and said taxane is selected from the group consisting of paclitaxel and docetaxel.

9. A therapeutically effective amount of a synergistic anticancer combined preparation, in which the cancer is sensitive to a synergistic combination, comprising a first compound and of a second compound, wherein:
the first compound is a 5-imino-13-deoxy anthracycline, or pharmaceutically acceptable salts or prodrugs thereof, said 5-imino-13-deoxy anthracycline having the formula:

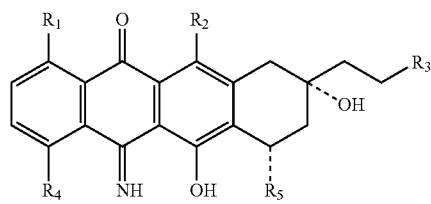

wherein
each $R_1$, $R_2$ and $R_3$ is independently selected from the group consisting of H and OH;
$R_4$ is selected from the group consisting of H, OH, alkyl, and O-alkyl;
$R_5$ is a sugar moiety; and
the second compound is a taxane.

10. The preparation of claim 9, wherein said 5-imino-13-deoxy anthracycline is selected from the group consisting of 5-imino-13-deoxydoxorubicin, 5-imino-13-deoxydaunorubicin, 5-imino-13-deoxycaminomycin, 5-imino-13-deoxyepirubicin, 5-imino-13-deoxyidarubicin, 5-imino-13-deoxyannamycin, and 5-imino-13-deoxyamrubicin, and said taxane is selected from the group consisting of paclitaxel and docetaxel.

11. A pharmaceutical composition comprising the preparation of claim 9, and a pharmaceutically acceptable carrier or excipient.

12. A pharmaceutical composition comprising the preparation of claim 10, and a pharmaceutically acceptable carrier or excipient.

13. The preparation of claim 9, wherein said sugar moiety is selected from the group consisting of daunosamine, epidaunosamine, and a rhamnal sugar.

14. A method for treating cancer which comprises administration to a mammal in need thereof a therapeutically effective amount of a synergistic combination comprising:
(a) a 5-imino-13-deoxyanthracycline, or pharmaceutically acceptable salts or prodrugs thereof, said 5-imino-13-deoxy anthracycline having the formula:

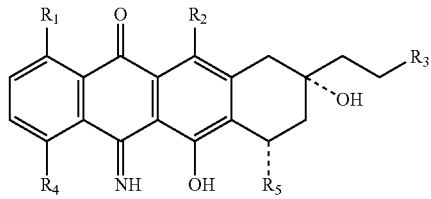

wherein
each $R_1$, $R_2$ and $R_3$ is independently selected from the group consisting of H and OH;
$R_4$ is selected from the group consisting of H, OH, alkyl, and O-alkyl;
$R_5$ is a sugar moiety; and
(b) a taxane, wherein the 5-imino-13-deoxyanthracycline and the taxane are administered simultaneously, separately, or sequentially to produce a synergistic anticancer effect, and wherein the cancer is sensitive to the synergistic combination.

15. The method of claim 14, wherein said sugar moiety is selected from the group consisting of daunosamine, epidaunosamine, and a rhamnal sugar.

16. The method of claim 14, wherein said 5-imino-13-deoxy anthracycline is selected from the group consisting of 5-imino-13-deoxydoxorubicin, 5-imino-13-deoxydaunorubicin, 5-imino-13-deoxycaminomycin, 5-imino-13-deoxyepirubicin, 5-imino-13-deoxyidarubicin, 5-imino-13-deoxyannamycin, and 5-imino-13-deoxyamrubicin, and said taxane is selected from the group consisting of paclitaxel and docetaxel.

17. The preparation of claim 1, wherein the preparation possesses an anti-cancer growth potency that is between 20 and 400 times higher than an anti-cancer growth potency of said taxane.

18. The preparation of claim 1 wherein said first compound is present in an amount that is lower than its therapeutically effective amount.

19. The preparation of claim 9 wherein said first compound is present in an amount that is lower than its therapeutically effective amount.

20. The method of claim 6 wherein said first compound is administered in an amount that is lower than its therapeutically effective amount.

21. The method of claim 14 wherein said first compound is administered in an amount that is lower than its therapeutically effective amount.

* * * * *